(12) United States Patent
Azizova et al.

(10) Patent No.: US 10,849,836 B2
(45) Date of Patent: Dec. 1, 2020

(54) COSMETIC COMPOSITION CAPABLE OF SIMULTANEOUSLY COLORING HAIR AND RELAXING CURLS

(71) Applicant: Zotos International, Inc., Darien, CT (US)

(72) Inventors: Marina Azizova, New Canaan, CT (US); Yanping Zhou, Blauvelt, NY (US); David Erlingheuser, Wallingford, CT (US); Rushi Tasker, Trumbull, CT (US)

(73) Assignee: Zotos International, Inc., Darien, CT (US)

( * ) Notice: Subject to any disclaimer, the term of this patent is extended or adjusted under 35 U.S.C. 154(b) by 0 days.

(21) Appl. No.: 15/183,210

(22) Filed: Jun. 15, 2016

(65) Prior Publication Data

US 2017/0360662 A1    Dec. 21, 2017

(51) Int. Cl.
| | |
|---|---|
| *A61K 8/19* | (2006.01) |
| *A61K 8/22* | (2006.01) |
| *A61Q 5/02* | (2006.01) |
| *A61Q 5/04* | (2006.01) |
| *A61Q 5/10* | (2006.01) |
| *A61Q 5/12* | (2006.01) |

(52) U.S. Cl.
CPC ............... *A61K 8/19* (2013.01); *A61K 8/22* (2013.01); *A61Q 5/02* (2013.01); *A61Q 5/04* (2013.01); *A61Q 5/10* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 3,651,931 A * | 3/1972 | Hsiung | A61K 8/368 222/94 |
| 4,732,990 A | 3/1988 | Login et al. | |
| 4,781,724 A | 11/1988 | Wajaroff et al. | |
| 5,188,639 A | 2/1993 | Schultz et al. | |
| 5,293,885 A | 3/1994 | Darkwa et al. | |
| 5,656,280 A | 8/1997 | Herb et al. | |
| 6,596,035 B2 | 7/2003 | Gutkowski et al. | |
| 2002/0192175 A1 | 12/2002 | Patel et al. | |
| 2004/0037796 A1 | 2/2004 | Collard et al. | |
| 2004/0042987 A1 | 3/2004 | Ulmer et al. | |
| 2004/0206368 A1 | 10/2004 | Warner et al. | |
| 2005/0191261 A1 | 9/2005 | Barbarat et al. | |
| 2005/0050656 A1 | 10/2005 | Huang et al. | |
| 2006/0182697 A1 | 8/2006 | Lalleman et al. | |
| 2008/0044369 A1 | 2/2008 | Rubin | |
| 2009/0047230 A1 | 2/2009 | Caballero et al. | |
| 2009/0297464 A1 | 12/2009 | Jegou | |
| 2012/0284932 A1 * | 11/2012 | Naoi | A61K 8/046 8/421 |
| 2013/0167861 A1 * | 7/2013 | Lopez | A61K 8/42 132/204 |
| 2015/0059794 A1 | 3/2015 | Rose et al. | |
| 2015/0290096 A1 | 10/2015 | Rose et al. | |

FOREIGN PATENT DOCUMENTS

| | | |
|---|---|---|
| CN | 1394588 A | 2/2003 |
| EP | 0328816 A2 | 8/1989 |
| EP | 2191864 A1 | 6/2010 |
| WO | 2002092036 A1 | 11/2002 |
| WO | 2009054931 A2 | 4/2009 |
| WO | 20144067702 A1 | 5/2014 |

OTHER PUBLICATIONS

International search report and written opinion for corresponding international application No. PCT/US 17/37656, 12 pages, dated Sep. 6, 2017.
International Preliminary Report on Patentability for the corresponding international application PCT/US17/37656, 14 pages, dated Jul. 12, 2018.
Extended European Search Report and European Search Opinion for the corresponding international application PCT/US17/37656, 8 pages, dated Dec. 12, 2019.

* cited by examiner

*Primary Examiner* — Nannette Holloman
(74) *Attorney, Agent, or Firm* — Ohlandt, Greeley, Ruggiero & Perle, L.L.P.

(57) ABSTRACT

A one step hair color and relaxer system comprising: an alkalizing agent in the range between about 0.1% to about 8%, based upon the total concentration of the hair color and relaxer system; a hair dye; and an oxidizing agent in the range between about 0.1% to about 6%, based upon the total concentration of the hair color and relaxer system; wherein the pH of the hair color and relaxer system is in the range between about 9 to about 14.

10 Claims, 4 Drawing Sheets

Left- Control    Right- single treatment

Left- Control    Right- single treatment, 1 shampoo

Left – Control   Right- 18 shampoos

MODEL A   Left – after air dry,   Right -after brushing

1ˢᵗ Application Result Summary

Prior to application   End results

MODEL B   Left —before service        Right —after service

MODEL C   Left before service        Right after service

COSMETIC COMPOSITION CAPABLE OF SIMULTANEOUSLY COLORING HAIR AND RELAXING CURLS

BACKGROUND

1. Field of the Disclosure

A novel one step dual benefit hair color and relaxer system (HCRS) that allows oxidative and direct dyes to penetrate the fiber of the hair to color and at the same time relax and smooth curly or unruly hair.

2. Discussion of the Background Art

The simultaneous dyeing and straightening of hair has been attempted for many decades with limited success and prior art is restricted to the use of direct dyes mixed into the hair straightening product due to the need to keep all of the oxidation reactive components segregated from the reducing agents of relaxers. The use of thiol or sulfite-based disulfide bond reducing technology is not possible in oxidative hair color systems due to the immediate reaction between the reducing agents and the oxidative agent (e.g., hydrogen peroxide) required by the oxidative hair dyes.

Traditional straightening effect is mainly based on the cleavage of disulfide bridges which are either reduced to Cysteine (especially in the presence of additional thiols), or form dehydroalanine in the presence of hydrogen sulfide. Most of the generated dehydroalanine reacts with cysteine to produce lanthionine. (Ref. http://publications.rwth-aachen.de/record/59435/files/04_094.pdf)

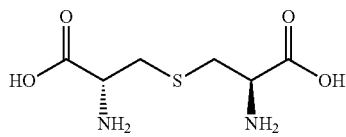

Lanthionine

This process is done at high pH and is damaging to hair.

Reduction

Reaction I: The Reduction of Disulfite Bond by LiOH can be Described by this Main Reaction Mechanism

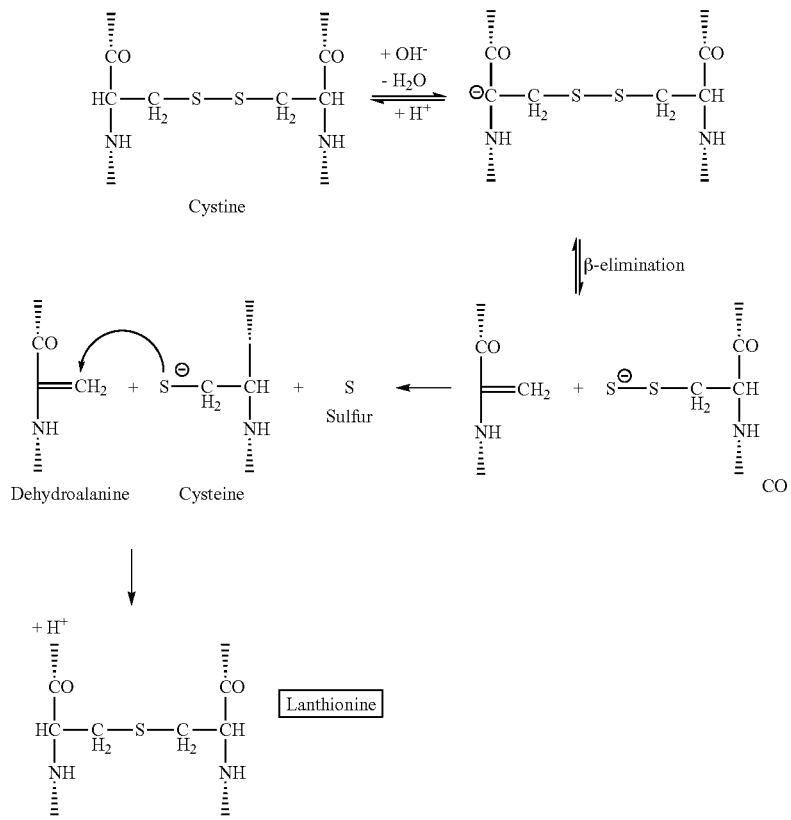

During this process, it is possible to deliver some semi-permanent hair dyes, as shown in prior art, but it is not possible to deliver permanent dyes to achieve good gray coverage and even color deposition.

The oxidative dyes require oxygen in order to start the reaction with hair keratin. Adding peroxide into the mixture negatively affects the straightening ability of a relaxer:

Oxidation

Reaction II: LiOH Gets Neutralized by the Oxidative Hydrogen Peroxide Molecule and is Unable to Reduce Hair.

$$LiOH + H_2O_2 \rightarrow LiOOH + H_2O$$

This explains why there are currently no commercial products that offer hair smoothing/taming and permanent color deposition/gray coverage.

Traditionally, hair relaxing and hair coloring with oxidative dyes are achieved as two independent processes, it is common to wait for 48 hours after relaxing prior to coloring hair. The ability to combine two processes would be a dramatic time saver for the consumer and hair stylist. An additional benefit to the consumer would be color that was first diminished by the traditional relaxing first step now would not be required to be enhanced by the coloring second step.

The present disclosure also provides many additional advantages, which shall become apparent as described below.

SUMMARY

In the present disclosure, the optimum combination of the active ingredients provides hair smoothing/relaxing while allowing oxidative dyes and direct hair dyes to penetrate hair to deposit color. The key technology finding behind the HCRS of the present disclosure is a specially designed hair color formula that contains optimum concentrations of alkalizing agent, mixed in situ with an oxidizer agent sufficient to deposit permanent oxidative color, while simultaneously relaxing unruly hair. The pH range for this product as applied to the hair ranges from about 9 to 14.

A 2 part one step hair color and relaxer and mixed oxidizing agent system comprising: part 1, an alkalizing agent in the range between about 0.1% to about 8%, based upon the total concentration of the hair color and relaxer system; a hair dye; and part 2 an oxidizing agent in the range between about 0.1% to about 6%, based upon the total concentration of the hair color and relaxer system; wherein the pH of the 2 part one step hair color and relaxer and mixed oxidizing agent system is in the range between about 9 to about 14.

The alkalizing agent is at least one selected from the group consisting of: lithium hydroxide, ammonium hydroxide, monoethanolamine, aminomethyl propanol, sodium hydroxide, potassium hydroxide, metal hydroxide blends, and other strong alkali.

The oxidizing agent is at least one selected from the group consisting of: hydrogen peroxide, urea peroxide, peroxyacids, sodium percarbonates, and sodium perborates.

The concentration of the alkalizing agent is more preferably in the range between about 1% to about 5%, most preferably between about 0.1% to about 3%.

The pH is more preferably in the range between about 10.5 to about 12.5 when mixed with the oxidizing agent.

The hair dye is at least one selected from the group consisting of: oxidative dyes and direct dyes.

The system further comprising conditioning agents with at least one selected from the group consisting of: cationic conditioning ingredients and oils.

A one step method for coloring and relaxing hair, the method comprises:
  applying hair color and relaxer system comprising: an alkalizing agent in the range between about 0.1% to about 8%, based upon the total concentration of the hair color and relaxer system; a hair dye; and an oxidizing agent in the range between about 0.1% to about 6%, based upon the total concentration of the hair color and relaxer system;
  wherein the pH of the 2 part hair color and relaxer and oxidizing system is in the range between about 9 to about 14.

The one step method further comprising blow drying the hair which has been treated with the hair color and relaxer system.

The one step method further comprising applying a flat iron to the blow dried hair, thereby assisting the hair to retain its straight shape.

The one step method further applying additional heat to the blow dried hair, thereby assisting the hair to retain its straight shape.

The one step method further comprising applying conditioning agents, shampoos and/or conditioners to further promote taming and relaxation of curls in the hair.

DETAILED DESCRIPTION OF THE PREFERRED EMBODIMENT

Figure 1:
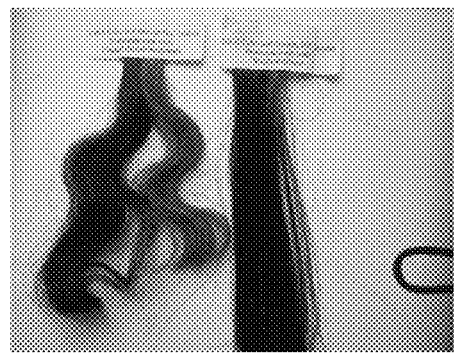
FIG. 1 is a photograph of a side-by-side study showing a control on the left which has only been dyed and the novel one step dual benefit hair color and relaxer system (HCRS) of the present disclosure on the right after a single treatment.
Figure 2:
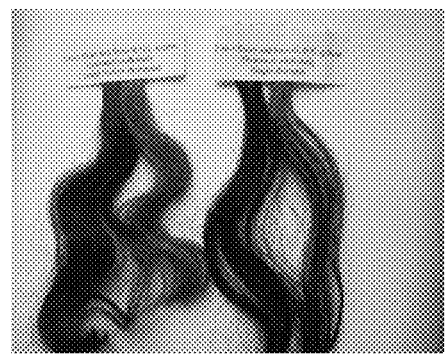
FIG. 2 is a photograph of a side-by-side study showing a control on the left which has only been dyed and the novel one step dual benefit hair color and relaxer system (HCRS) of the present disclosure on the right after a single treatment and one shampoo.
Figure 3:
FIG. 3 is a photograph of a side-by-side study showing a control on the left which has only been dyed and the novel one step dual benefit hair color and relaxer system (HCRS) of the present disclosure on the right after a single treatment and after six shampoos.
Figure 4:
FIG. 4 is a photograph of a side-by-side study showing a control on the left which has only been dyed and the novel one step dual benefit hair color and relaxer system (HCRS) of the present disclosure on the right after a single treatment and after twelve shampoos.
Figure 5:
FIG. 5 is a photograph of a side-by-side study showing a control on the left which has only been dyed and the novel one step dual benefit hair color and relaxer system (HCRS) of the present disclosure on the right after a single treatment and after eighteen shampoos.

The present inventors have unexpectedly discovered that a one step process which simultaneously and permanently de-frizz hair, relax curls and deposit permanent hair color is, in fact, possible.

It was discovered that by mixing, for example, LiOH and $H_2O_2$ in a specific concentration and pH ranges, a unique oxidative hair coloring, smoothing, defrizzing and curl relaxing product can be formed. Key components of this hair color and relaxer system, include, but are not limited to:

alkalizing agent (e.g., lithium hydroxide, ammonium hydroxide, monoethanolamine, aminomethyl propanol, sodium hydroxide, potassium hydroxide, metal hydroxide blends, and other strong alkali) around in a concentration range between about 0.1% to about 8%, by weight, of the hair color and relaxer system, more preferably between about 1% to about 5%, most preferably about 3% to about 5%;

an oxidizer agent, e.g., hydrogen peroxide, having a concentration range between about 0.1% to about 6%, by weight, of the hair color and relaxer system, more preferably between about 0.1% to about 3%, most preferably about 1% to about 2%; and an oxidative dye or combinations of oxidative and direct dyes having a concentration range between about 0.5 to about 20%, by weight, of the hair color and relaxer system, more preferably between about 1% to about 15%, most preferably about 1.5% to about 10%.

It is preferred that the hair color and relaxer system have a pH range between about 9 to about 14, more preferably between about 10.0 to about 13, most preferably about 10.5 to about 12.

With the preferred concentration range of the alkalizing agent, we are able to soften the cysteine and form cysteic acid via a hydrogen peroxide oxidation pathway. This is also a preferred pathway for elimination of lanthionine formation as lanthionine formation is usually associated with significant hair damage.

In this process, hair keratin gets softened by LiOH forming cysteic acid while making the hair very receptive to dye deposition.

Reaction III: Cysteic Acid Formation

When applied to hair, LiOH reacts with di-sulfide bond in cystine to form small amounts of sulfenic acid which is easily oxidized by peroxide to form cysteic acid as shown below:

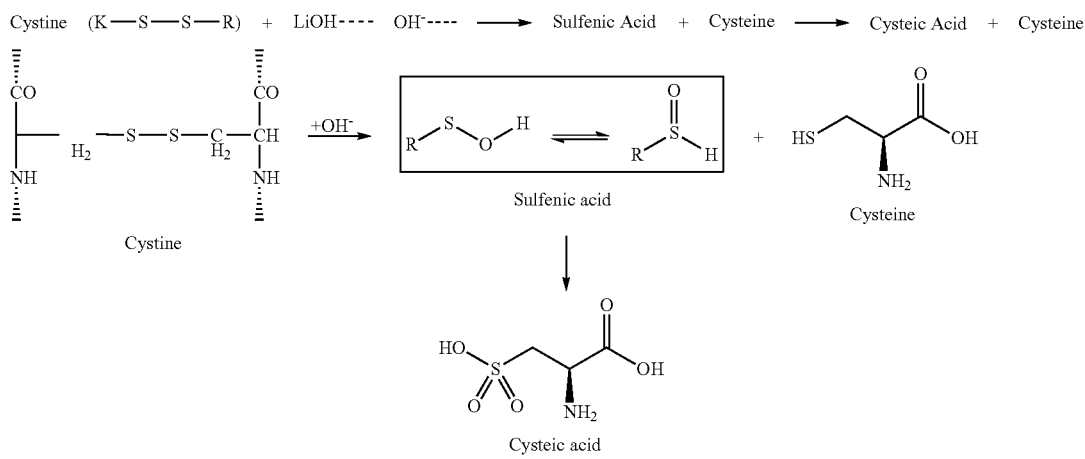

This reaction was confirmed by the measured increase of cysteic acid in test hair swatches as will be shown below.

Evaluation of Reducing Agents

Various reducing agents were evaluated to determine optimum curl relaxation from the hair color and relaxer system of the present disclosure.

TABLE 1

(Selection of reducing agent suitable to work in a hair color formula)

| | Traditional Demi color | Sodium Sulfite | Ammonium Sulfite | Potassium Carbonate | Lithium Hydroxide | Ammonium Thioglycolate | Traditional Relaxer |
|---|---|---|---|---|---|---|---|
| % Reducing Agent | 0% | 3.00% | 3.00% | 3.00% | 2.70% | 2.00% | 4% |
| Mixed pH | 9.83 | 9.85 | 9.88 | 9.92 | 10.88 | 9.20 | 12, No mixing |
| Levels of deposit | 1 - control | ¼ | 1 | ½ | ½ | ¼ | none |
| Curl relaxation* | 1 | 1 | 1 | 1 | 3 | 2 | 5 |
| Temperature of mixture | 24.3° C. | 24.5° C. | 31.8° C. | 25.2° C. | 24.5° C. | 30.8° C. | n/a |
| Overall Comments | Color Control | low effect | temp rise and low effect | low straightening effect | best option | 7° C. temp rise and high odor | Smoothing control |

*Rated on the scale 1 - poor (no effect) . . . 5 - excellent (full relaxation)

The color results produced by products made with various reducing materials were evaluated on hair swatches by an expert panel. The positive control in this case was the traditional hair color. The negative control was a traditional relaxer that did not deposit the color at all, but removed the existing color, making hair appear lighter, which is an undesirable effect. Most reducing agents were inferior to traditional demi color in their color deposition. Thus, this type of a system needs to have different color pallet to provide the desirable hair color deposit.

Curl relaxation is the second key benefit of the hair color and relaxer system of the present disclosure. It was one object of the present disclosure to also identify the most suitable reducing agent to be used in the hair color and relaxer system to achieve the most curl relaxation. The relaxation was evaluated by the expert panel on the scale of 1 to 5. Traditional hair color was used as a negative control and designated as '1', while traditional relaxer was presented as a positive control and was designated as '5'. Lithium hydroxide and ammonium thioglycolate gave notable improvement over traditional hair color and were rated above '1'. Lithium hydroxide was more available to complete a higher degree of curl relaxation. Amonium thioglycolate consumed the hydrogen peroxide yielding the same curl relaxation but with very poor color formation and deposit. Ammonium thioglycolate also gave a significant temperature rise.

Many agents used for hair relaxing without hydrogen peroxide, can produce heat when reacting with hydrogen peroxide. The heat is undesirable as it may irritate the scalp and sometimes even dangerous as the clients can get burned with the product mixture. Table 1 shows that ammonium sulfite and ammonium thioglycolate can experience 5 to 7 degree temperature rises as compared to the traditional hair color. Lithium hydroxide did not result in any significant temperature rise.

Overall, LiOH was the preferred embodiment to relax/defrizz hair under oxidative (e.g., hydrogen peroxide) environment with relaxing and fizz reductions effects. The relaxing of fiber indicates that cysteine was reduced, thereby allowing for the relaxing/defrizzing of the fiber.

Once lithium hydroxide was identified as the leading candidate for the hair color and relaxer system based on the experiments above, the concentrations needed to be optimized to balance performance as a relaxing agent while minimizing the impact on the color uptake and hair damage.

TABLE 2

(Optimization of LiOH concentration to maximize degree of hair relaxation and dye uptake)

|  | initial | 1% LiOH | 4% LiOH* | 5% LiOH* | 6% LiOH* | 7% LiOH* | 8% LiOH* |
|---|---|---|---|---|---|---|---|
| swatch length (cm) | 12.00 | 12.6 | 14.10 | 14.30 | 14.40 | 14.40 | 14.30 |
| increased % | n/a | 5% | 17.5 | 19.2 | 20.0 | 20.0 | 19.2 |
| color results (deposition) | control | 2 levels darker | 2 levels darker | 1 level darker | 1 level darker | ½ levers darker vs. initial | ½ levers darker vs. initial |

*In this experiment LiOH was used in a mono-hydrate formula (LiOH*$H_2O$)

The relaxation effect showed to be directly proportional to the concentration of LiOH in the mixture. Lithium hydroxide purchased for this experiment was used in a monohydrate formula (LiOH*$H_2O$). The concentration based on the raw material specification is LiOH*H2O—minimum 56.5% active.

We have explored and tested multiple concentrations, e.g., 7% LiOH mono-hydrate, is approximately 4% active in-base, and when mixed 1:1=2% on head and 4% LiOH mono-hydrate equates to 2.3% in base, when mixed 1:1=1.1% on head, both work well. Going below 4%, proved to be of little value @ 1.1% on head below traditional mild relaxers (TBC) to produce visible result. The concentration of 4% of LiOH*$H_2O$ in the formula provides minimal decrease in color uptake.

Table 2 supports conditions for max color deposition and maximum relaxation of curly hair. We believe that excess LiOH is neutralized by hydrogen peroxide reducing color uptake but provides maximum curl deformation. At 4% (i.e. 1.1% LiOH on head)—max color with moderate curl deformation is achieved. The working mixture pH range of between about 10.5 to about 12 is critical to have this reaction mechanism.

TABLE 3

(Optimization of Developer to maximize hair relaxing effectiveness, dye uptake and hair conditions)

| Developer Volume | RTA pH | Developer | Initial swatch length (cm) | Swatch length after 1st application (cm) | increased length % | hair color comment | condition of the hair |
|---|---|---|---|---|---|---|---|
| 10 Vol | 10.10 | 10 Vol | 13.90 | 14.60 | 5.04 | darkest | nice in shape & feel |
| 5 Vol | 10.33 | 5 Vol | 13.70 | 14.30 | 4.38 | ½ to ¾ level lighter | nice in shape & feel |
| 4 Vol | 10.42 | 4 Vol | 13.10 | 14.40 | 9.92 | ¼ to ½ level lighter | nice in shape & feel |
| 3 Vol | 10.52 | 3 Vol | 13.30 | 14.50 | 9.02 | ½ to ¾ level lighter | nice in shape & feel |
| 0 Vol | 11.02 | 0 Vol | 13.80 | 13.90 | 0.72 | lightest | nice in shape & feel |

The maximum increase in swatch length, most relaxation, was achieved at 4 Volume (i.e. 1.2% peroxide). Although higher volume developer provided more color deposit and would be better for coloring of hair, the 4 Vol developer provided maximum hair relaxation without significant decrease in the color uptake.

Once the formula and developer were optimized, the optimal combination was applied to hair to evaluate potential damage to the critical amino acids. Traditional hair color formula and hair relaxers were used as positive and negative controls. Untreated hair was analyzed as a baseline.

When hair is treated with a chemical relaxer, hair cystine is cleaved, and a new crosslink, the lanthionine, is subsequently formed to help stabilize the hair in the straight configuration. Lanthionine is a major reaction product between metal alkali and cysteine.

However, as shown above, we have observed that permanent hair straightening is possible without lanthionine formation. The narrow range of LiOH allowed us to achieve the straightening and smoothing without forming lanthionine. The analysis of amino acid content below show that the hair color and relaxer system of the present disclosure with LiOH and low volume developer can produce curl relaxation without lanthionine formation.

TABLE 5

(Evaluation of hair internal conditions via Amino acid analysis of Cysteic Acid, Cystine and Lanthionine)

| Treatment | Cysteic Acid Umol/g Hair | % Increase Cysteic Acid | Cystine umol/g Hair | % Decrease Cystine | Lanthionine Umol/g Hair | Notes |
|---|---|---|---|---|---|---|
| Baseline Control: Brown Curly Hair | 29 | | 460 | | | Baseline |
| 1 (x) Traditional Hair color mixture. 5N Washed 10X with 10% SLES | 52 | 79% | 430 | 7% | | Positive Control |
| 1 (x) HCRS technology pH10.8; Washed 10X with 10% SLES | 45 | 55% | 429 | 7% | | OPTIMAL |
| 1 (x) HCRS technology pH11.8; Washed 10X with 10% SLES | 72 | 148% | 403 | 12% | | OPTIMAL |
| 1 (x) HCRS technology - No Developer; Washed 10X with 10% SLES | 34 | 17% | 404 | | 5 | Lanthionine formed without use of developer |
| 1 (x) Guanidine/OH Relaxer; Washed 10X with 10% SLES | 40 | 38% | 384 | 17% | 13 | Negative Control |
| 1 (x) LiOH Relaxer; Washed 10X with 10% SLES | 36 | 24% | 387 | 16% | 14 | Negative Control |

The above study showed that the pH of the hair color and relaxer system of the present disclosure is critical and can increase cysteic acid and prevent the lanthionine formation associated with amino acid damage to hair. The target hair color and relaxer system formulation provides hair damage similar to that of traditional hair color technology and can operate in pH range of between about 10.5 to about 12.

Listed below are examples of hair color and relaxer system formulations according to the present disclosure:

Example 1

HCRS Hair Color and Relaxer System "Light Brown" with 4% LiOH

| The INCI Name | % |
|---|---|
| Water | qs |
| Mineral Oil | 5.0000 |
| Oleyl Alcohol | 3.000 |
| Polysorbate 80 | 0.1000 |
| Cetearyl alcohol | 3.4000 |
| Stearic Acid | 1.5000 |
| Glyceryl Stearate | 1.5000 |
| Steareth-21 | 3.5000 |
| Glycol Distearate | 0.8000 |
| Stearamidopropyl Dimethylamine | 1.5000 |
| Glycine Soja Oil | 2.0000 |
| Propylene Glycol | 3.0000 |
| Tetrasodium EDTA | 0.1500 |
| Sodium Sulfite | 0.6000 |
| Sodium Metasilicate | 0.0500 |
| Lithium Hydroxide | 4.0000 |
| p-Phenylenediamine | 0.4000 |
| p-Aminophenol | 0.0500 |
| N,N-Bis(2-Hydroxyethyl-p-Phenylenediamine Sulfate | 0.4500 |
| m-Aminophenol | 0.1100 |
| 1-Naphthol | 0.0420 |
| 2-Methylresorcinol | 0.0880 |
| Resorcinol | 0.6800 |
| 2-nitro-paraphenylenediamine | 0.0100 |
| Decyl Glucoside | 1.0000 |
| Sodium Methyl Cocoyl Taurate | 1.0000 |
| Fragrance | 0.6000 |
| Ammonium Hydroxide | 0.1000 |

Example 2

HCRS Hair Color and Relaxer System "Light Brown" with 4% LiOH

| The INCI Name | % |
|---|---|
| Water | qs |
| Mineral Oil | 5.0000 |
| Oleyl Alcohol | 3.000 |
| Cetearyl alcohol | 3.4000 |
| Stearic Acid | 3.5000 |
| Steareth-21 | 1.5000 |
| Stearamidopropyl Dimethylamine | 1.5000 |
| Glycine Soja Oil | 2.0000 |
| Propylene Glycol | 3.0000 |
| Tetrasodium EDTA | 0.1500 |
| Sodium Sulfite | 0.6000 |
| Sodium Metasilicate | 0.0500 |
| Lithium Hydroxide | 4.0000 |
| p-Phenylenediamine | 0.3800 |
| m-Aminophenol | 0.0150 |
| 1-Hydroxyethyl 4,5-Diamino Pyrazole Sulfate | 1.1500 |
| 5-Amino-6-Chloro-o-Cresol | 0.0400 |
| Decyl Glucoside | 6.0000 |
| Fragrance | 0.6000 |
| Ammonium Hydroxide | 2.0000 |

Example 3

HCRS System "Developer"

| The INCI Name | % |
|---|---|
| Water | qs |
| Mineral Oil | 0.6000 |
| Squalane | 0.5000 |
| Cetearyl Alcohol | 2.85000 |
| Ceteth-20 | 0.1000 |
| Sodium Stannate | 0.0200 |
| Phosphoric Acid | 0.0500 |
| Disodium Phosphate | 0.0200 |
| Hydrogen Peroxide, 50% | 3.0000 |

Laboratory Results Hair Swatches Evaluations

The hair color and relaxer system of the present disclosure was analyzed first in the research and development laboratory using untreated curly and wavy hair. The performance of this system was tested against an existing hair color formula.

Durability Evaluation.

The swatches were prepared as follows:

Control (just curly/wavy hair), single shampoo, 6, 12, 18, and 24 shampoos

The swatches were then (all) dyed-out for 30 minutes, rinsed, blow dried, and flat ironed using a flat iron. The swatches were then left for 24 hours for the process to settle.

The swatches were then washed to the designated amount of shampoos on the label of each swatch and just blow dried.

The side-by-side study showed that 2-in-1 color and smooth did relax curl/wavy, smooth frizzy, and calm unruly hair after between 1 and 18 shampoos. Swatches that were dyed out using ordinary hair color did not relax curly/wavy, smooth frizzy, or calm unruly hair, as shown on the Left-Control of FIGS. 1-6.

The hair color and relaxer system treatment gives long lasting color and relaxing of curl. It was also found very beneficial to use heat styling tools to further straighten and relax curls. It is known that heat improves reformation of hydrogen bond and in conjunction with the hair color and relaxer system enhances cysteine reduction/oxidation reaction, which results in smoother hair.

Based on the laboratory evaluation it is obvious that while results may vary based on the concentration of active ingredients, the changes made to hair using hair color and relaxer system of the present disclosure are permanent.

Salon Evaluations of the Hair Color and Relaxer System, in Test Salon

Figure 6:
FIG. 6 is a photograph of a side-by-side study showing a non-treated Model A on the left and Model A after treatment of her hair with the novel one step dual benefit hair color and relaxer system (HCRS) of the present disclosure on the right after air dry and brushing.
Figure 6:
Figure 7:
FIG. 7 is a photograph of a side-by-side study showing a non-treated Model B on the left and Model B after treatment of her hair with the novel one step dual benefit hair color and relaxer system (HCRS) of the present disclosure on the right after air dry and brushing.
Figure 8:
FIG. 8 is a photograph of a side-by-side study showing a non-treated Model C on the left and Model C after treatment of her hair with the novel one step dual benefit hair color and relaxer system (HCRS) of the present disclosure on the right after air dry and brushing.

FIGS. 6-8 show the beneficial effects that the hair color and relaxer system of the present disclosure have when applied to the respective hair of Models A, B and C.

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

What is claimed is:

1. A one step hair color and relaxer system comprising:
about 0.1% to about 8%, based upon the total concentration of the hair color and relaxer system, of an alkalizing agent selected from the group consisting of lithium hydroxide, sodium hydroxide, and potassium hydroxide, and any combinations thereof;
at least one hair dye, wherein said hair dye is at least one selected from the group consisting of oxidative dyes and direct dyes; and
an oxidizing agent in the range between about 1% to about 2%, based upon the total concentration of the hair color and relaxer system;
wherein said pH of the hair color and relaxer system is in the range between about 9 to about 14.

2. The system according to claim 1, further comprising at least one component selected from the group consisting of ammonium hydroxide, monoethanolamine, aminomethyl propanol, metal hydroxide blends, other strong alkali, and any combinations thereof.

3. The system according to claim 1, wherein said oxidizing agent is at least one selected from the group consisting of: hydrogen peroxide, urea peroxide, peroxyacids, sodium percarbonates, and sodium perborates.

4. The system according to claim 1, wherein said alkalizing agent is in the range between about 1% to about 5%.

5. The system according to claim 4, wherein said alkalizing agent is in the range between about 3% to about 5%.

6. The system according to claim 1, wherein said pH is in the range between about 10.5 to about 12.

7. The system according to claim 1, further comprising at least one conditioning agent.

8. The system according to claim 7, wherein said conditioning agent is at least one selected from the group consisting of: cationic conditioning ingredients and oils.

9. A one step hair color and relaxer system comprising:
about 1% to about 5%, based upon the total concentration of the hair color and relaxer system, of an alkalizing agent selected from the group consisting of lithium hydroxide, sodium hydroxide, and potassium hydroxide, and any combinations thereof;
at least one hair dye, wherein said hair dye is at least one selected from the group consisting of oxidative dyes and direct dyes; and
an oxidizing agent in the range between about 1% to about 2%, based upon the total concentration of the hair color and relaxer system;
wherein said pH of the hair color and relaxer system is in the range between about 9 to about 14.

10. The system according to claim 9, further comprising at least one component selected from the group consisting of ammonium hydroxide, monoethanolamine, aminomethyl propanol, metal hydroxide blends, other strong alkali, and any combinations thereof.

* * * * *